United States Patent
Zhou et al.

(10) Patent No.: US 8,137,293 B2
(45) Date of Patent: Mar. 20, 2012

(54) GUIDEWIRES INCLUDING A POROUS NICKEL-TITANIUM ALLOY

(75) Inventors: Pu Zhou, Maple Grove, MN (US); Horng-Ban Lin, Maple Grove, MN (US); Hancun Chen, Maple Grove, MN (US); James Feng, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 52 days.

(21) Appl. No.: 12/620,343

(22) Filed: Nov. 17, 2009

(65) Prior Publication Data

US 2011/0118628 A1 May 19, 2011

(51) Int. Cl.
- *A61B 5/00* (2006.01)
- *A61M 25/00* (2006.01)
- *C22C 28/00* (2006.01)
- *C22C 19/05* (2006.01)

(52) U.S. Cl. .................. 600/585; 420/417; 420/446
(58) Field of Classification Search .................. 420/451, 420/417, 441; 600/585; 148/402, 426, 421, 148/902, 909
See application file for complete search history.

(56) References Cited

U.S. PATENT DOCUMENTS

| | | | |
|---|---|---|---|
| 1,553,227 A | 9/1925 | Feyk et al. | |
| 1,866,888 A | 7/1932 | Hawley | |
| 2,275,827 A | 3/1942 | Plensler | |
| 2,413,805 A | 1/1947 | Vickers | |
| 2,441,166 A | 5/1948 | Raspert | |
| 2,561,890 A | 7/1951 | Stoddard | |
| 2,722,614 A | 11/1955 | Fryklund | |
| 2,857,536 A | 10/1958 | Light | |
| 2,864,017 A | 12/1958 | Waltscheff | |
| 2,871,793 A | 2/1959 | Michie et al. | |
| 3,249,776 A | 5/1966 | Anderson et al. | |
| 3,322,984 A | 5/1967 | Anderson | |
| 3,334,253 A | 8/1967 | Hill | |
| 3,363,470 A | 1/1968 | Yavne | |
| 3,452,227 A | 6/1969 | Welch | |
| 3,452,742 A | 7/1969 | Muller | |
| 3,463,953 A | 8/1969 | Maxwell | |
| 3,512,019 A | 5/1970 | Durand | |

(Continued)

FOREIGN PATENT DOCUMENTS

EP 0 215 173 3/1987

(Continued)

OTHER PUBLICATIONS

"Mechanical Design and Systems Handbook", H.A. Rothbart, 1964, p. 33-13 (one sheet).

(Continued)

*Primary Examiner* — Max Hindenburg
*Assistant Examiner* — Charles Becker
(74) *Attorney, Agent, or Firm* — Seager, Tufte & Wickhem, LLC (57) ABSTRACT

Medical devices and methods for making and using the same are disclosed. An example medical device may include a guidewire. The guidewire may include an elongate shaft. The shaft may include a porous metal alloy. The porous metal alloy may be arranged so that the porous metal alloy has a first pore distribution along a first portion of the shaft and a second pore distribution different from the first pore distribution along a second portion of the shaft.

17 Claims, 6 Drawing Sheets

U.S. PATENT DOCUMENTS

| | | |
|---|---|---|
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Willson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,582,536 A * | 4/1986 | Raybould .................. 75/246 |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,973,321 A | 11/1990 | Michelson |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gambale |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,228,453 A | 7/1993 | Sepetka |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,340,533 A | 8/1994 | Stangle et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,049 A | 11/1994 | Raman et al. |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,409,015 A | 4/1995 | Palermo |
| 5,411,476 A | 5/1995 | Abrams |
| 5,425,723 A | 6/1995 | Wang |
| 5,437,288 A * | 8/1995 | Schwartz et al. ............. 600/585 |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,460,187 A | 10/1995 | Daigle et al. |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |

| Patent | Date | Inventor |
|---|---|---|
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |
| 5,605,543 A | 2/1997 | Swanson |
| 5,622,184 A | 4/1997 | Ashby et al. |
| 5,630,806 A | 5/1997 | Inagaki et al. |
| 5,637,089 A | 6/1997 | Abrams et al. |
| 5,656,011 A | 8/1997 | Uihlein et al. |
| 5,658,264 A | 8/1997 | Samson et al. |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk |
| 5,676,697 A | 10/1997 | McDonald |
| 5,682,894 A | 11/1997 | Orr et al. |
| 5,690,120 A | 11/1997 | Jacobsen et al. |
| 5,720,300 A | 2/1998 | Fagan et al. |
| 5,722,609 A | 3/1998 | Murakami |
| 5,728,063 A | 3/1998 | Preissman et al. |
| 5,741,429 A | 4/1998 | Donadio, III et al. |
| 5,746,701 A | 5/1998 | Noone |
| 5,769,830 A | 6/1998 | Parker |
| 5,772,609 A | 6/1998 | Nguyen et al. |
| 5,782,809 A | 7/1998 | Umeno et al. |
| 5,788,653 A | 8/1998 | Lorenzo |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,810,885 A | 9/1998 | Zinger |
| 5,813,996 A | 9/1998 | St. Germain et al. |
| 5,827,225 A | 10/1998 | Ma Schwab |
| 5,827,242 A | 10/1998 | Follmer et al. |
| 5,833,632 A | 11/1998 | Jacobsen et al. |
| 5,836,926 A | 11/1998 | Peterson et al. |
| 5,843,050 A | 12/1998 | Jones et al. |
| 5,843,244 A | 12/1998 | Pelton et al. |
| 5,851,203 A | 12/1998 | van Muiden |
| 5,895,378 A | 4/1999 | Nita |
| 5,897,537 A | 4/1999 | Berg et al. |
| 5,902,254 A | 5/1999 | Magram |
| 5,902,290 A | 5/1999 | Peacock, III et al. |
| 5,902,499 A | 5/1999 | Richerzhagen |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone |
| 5,916,194 A | 6/1999 | Jacobsen et al. |
| 5,931,830 A | 8/1999 | Jacobsen et al. |
| 5,935,108 A | 8/1999 | Katoh et al. |
| 5,947,940 A | 9/1999 | Beisel |
| 5,951,539 A | 9/1999 | Nita et al. |
| 5,955,640 A | 9/1999 | Paludetto et al. |
| 5,971,975 A | 10/1999 | Mills et al. |
| 5,980,471 A | 11/1999 | Jafari |
| 5,997,487 A | 12/1999 | Kolehmainen et al. |
| 6,001,068 A | 12/1999 | Uchino et al. |
| 6,004,279 A | 12/1999 | Crowley et al. |
| 6,007,478 A | 12/1999 | Siess et al. |
| 6,014,919 A | 1/2000 | Jacobsen et al. |
| 6,017,319 A | 1/2000 | Jacobsen et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,042,553 A | 3/2000 | Solar et al. |
| 6,045,547 A | 4/2000 | Ren et al. |
| 6,048,339 A | 4/2000 | Zirps et al. |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,071,305 A | 6/2000 | Brown et al. |
| 6,106,485 A | 8/2000 | McMahon |
| 6,106,488 A | 8/2000 | Fleming et al. |
| 6,139,510 A | 10/2000 | Palermo |
| 6,165,292 A | 12/2000 | Abrams et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| RE37,148 E | 4/2001 | Shank |
| 6,214,042 B1 | 4/2001 | Jacobsen et al. |
| 6,228,073 B1 | 5/2001 | Noone et al. |
| 6,248,082 B1 | 6/2001 | Jafari |
| 6,251,092 B1 | 6/2001 | Qin et al. |
| 6,254,549 B1 | 7/2001 | Ramzipoor |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,273,879 B1 | 8/2001 | Keith et al. |
| 6,290,656 B1 | 9/2001 | Boyle et al. |
| 6,296,616 B1 | 10/2001 | McMahon |
| 6,296,631 B2 | 10/2001 | Chow |
| 6,296,667 B1 | 10/2001 | Johnson et al. |
| 6,302,870 B1 | 10/2001 | Jacobsen et al. |
| 6,325,790 B1 | 12/2001 | Trotta |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,005 B1 | 3/2002 | Powell et al. |
| 6,355,027 B1 | 3/2002 | Le et al. |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,383,146 B1 | 5/2002 | Klint |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen |
| 6,478,778 B1 | 11/2002 | Jacobsen et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,503,244 B2 | 1/2003 | Hayman |
| 6,508,803 B1 | 1/2003 | Horikawa et al. |
| 6,524,301 B1 | 2/2003 | Wilson et al. |
| 6,530,934 B1 | 3/2003 | Jacobsen et al. |
| 6,547,779 B2 | 4/2003 | Levine et al. |
| 6,553,880 B2 | 4/2003 | Jacobsen et al. |
| 6,556,873 B2 | 4/2003 | Smits |
| 6,579,246 B2 | 6/2003 | Jacobsen et al. |
| 6,602,207 B1 | 8/2003 | Mam et al. |
| 6,602,280 B2 | 8/2003 | Chobotov |
| 6,610,046 B1 | 8/2003 | Usami et al. |
| 6,623,448 B2 | 9/2003 | Slater |
| 6,636,758 B2 | 10/2003 | Sanchez et al. |
| 6,638,266 B2 | 10/2003 | Wilson et al. |
| 6,652,508 B2 | 11/2003 | Griffin et al. |
| 6,673,025 B1 | 1/2004 | Richardson et al. |
| 6,682,493 B2 | 1/2004 | Mirigian |
| 6,689,120 B1 | 2/2004 | Gerdts |
| 6,702,762 B2 | 3/2004 | Jafari et al. |
| 6,712,826 B2 | 3/2004 | Lui |
| 6,730,095 B2 | 5/2004 | Olson, Jr. et al. |
| 6,749,560 B1 | 6/2004 | Konstorum et al. |
| 6,766,720 B1 | 7/2004 | Jacobsen et al. |
| 6,777,644 B2 | 8/2004 | Peacock, III et al. |
| 6,811,544 B2 | 11/2004 | Schaer |
| 6,837,898 B2 | 1/2005 | Boyle et al. |
| 6,866,642 B2 | 3/2005 | Kellerman et al. |
| 6,887,235 B2 | 5/2005 | O'Connor et al. |
| 6,918,882 B2 | 7/2005 | Skujins et al. |
| 6,997,937 B2 | 2/2006 | Jacobsen et al. |
| 7,001,369 B2 | 2/2006 | Griffin et al. |
| 7,071,197 B2 | 7/2006 | Leonardi et al. |
| 7,074,197 B2 | 7/2006 | Reynolds et al. |

| | | | | | | |
|---|---|---|---|---|---|---|
| 7,153,277 | B2 | 12/2006 | Skujins et al. | GB | 2257269 | 1/1993 |
| 7,169,118 | B2 | 1/2007 | Reynolds et al. | JP | 58-8522 | 1/1983 |
| 7,182,735 | B2 | 2/2007 | Shireman et al. | JP | 62-299277 | 12/1987 |
| 7,618,379 | B2 | 11/2009 | Reynolds et al. | JP | 1-135363 | 5/1989 |
| 7,708,704 | B2 * | 5/2010 | Mitelberg et al. ............. 600/585 | JP | 1-158936 | 6/1989 |
| 2002/0019599 | A1 | 2/2002 | Rooney et al. | JP | 2-107268 | 4/1990 |
| 2003/0009208 | A1 | 1/2003 | Snyder et al. | JP | 03-122850 | 12/1991 |
| 2003/0060732 | A1 | 3/2003 | Jacobsen et al. | JP | 4-061840 | 2/1992 |
| 2003/0069522 | A1 | 4/2003 | Jacobsen et al. | JP | 5-506806 | 10/1993 |
| 2003/0216668 | A1 | 11/2003 | Howland et al. | JP | 5-309519 | 11/1993 |
| 2004/0059257 | A1 * | 3/2004 | Gaber ........................ 600/585 | JP | 6-31749 | 4/1994 |
| 2004/0116831 | A1 | 6/2004 | Vrba | JP | 6-63224 | 9/1994 |
| 2004/0142643 | A1 | 7/2004 | Miller et al. | JP | 6-312313 | 11/1994 |
| 2004/0167437 | A1 | 8/2004 | Sharrow et al. | JP | 7-124164 | 5/1995 |
| 2004/0167441 | A1 | 8/2004 | Reynolds et al. | JP | 7-124263 | 5/1995 |
| 2004/0181174 | A2 | 9/2004 | Davis et al. | JP | 7-136280 | 5/1995 |
| 2004/0181176 | A1 | 9/2004 | Jafari et al. | JP | 7148264 | 6/1995 |
| 2005/0115624 | A1 | 6/2005 | Walak | JP | 7037199 | 7/1995 |
| 2006/0121218 | A1 | 6/2006 | Obara et al. | JP | 7185009 | 7/1995 |
| 2006/0189896 | A1 | 8/2006 | Davis et al. | JP | 7275366 | 10/1995 |
| 2006/0264904 | A1 | 11/2006 | Kerby et al. | JP | 751067 | 11/1995 |
| 2007/0100285 | A1 | 5/2007 | Griffin et al. | JP | 8509141 | 10/1996 |
| 2007/0100374 | A1 | 5/2007 | Vrba | JP | 8-317988 | 12/1996 |
| 2007/0100424 | A1 | 5/2007 | Chew et al. | JP | H9-164 | 4/1997 |
| 2007/0142817 | A1 * | 6/2007 | Hurt .............................. 604/508 | JP | 9-276413 | 10/1997 |
| 2008/0021347 | A1 | 1/2008 | Jacobsen et al. | JP | 10-118193 | 5/1998 |
| 2008/0021348 | A1 | 1/2008 | Jacobsen et al. | JP | 2000-197704 A | 7/2000 |
| 2008/0021400 | A1 | 1/2008 | Jacobsen et al. | WO | WO 90/02520 | 3/1990 |
| 2008/0021401 | A1 | 1/2008 | Jacobsen et al. | WO | WO 95/32834 | 12/1995 |
| 2008/0021402 | A1 | 1/2008 | Jacobsen et al. | WO | WO 96/38193 | 12/1996 |
| 2008/0021403 | A1 | 1/2008 | Jacobsen et al. | WO | WO 97/44086 | 11/1997 |
| 2008/0021404 | A1 | 1/2008 | Jacobsen et al. | WO | WO 99/11313 | 3/1999 |
| 2008/0021405 | A1 | 1/2008 | Jacobsen et al. | WO | WO 02/13682 | 2/2002 |
| 2008/0021406 | A1 | 1/2008 | Jacobsen et al. | WO | WO 2004/047899 | 6/2004 |
| 2008/0021407 | A1 | 1/2008 | Jacobsen et al. | | | |
| 2008/0021408 | A1 | 1/2008 | Jacobsen et al. | | | |
| 2008/0064989 | A1 | 3/2008 | Chen et al. | | | |
| 2008/0077119 | A1 | 3/2008 | Snyder et al. | | | |
| 2009/0043283 | A1 | 2/2009 | Turnlund et al. | | | |

FOREIGN PATENT DOCUMENTS

| | | |
|---|---|---|
| EP | 0 377 453 | 7/1990 |
| EP | 0 778 039 | 6/1997 |
| EP | 0 937 481 | 8/1999 |
| EP | 0 790 066 | 4/2000 |
| EP | 0 608 853 | 4/2003 |

OTHER PUBLICATIONS

Information printed from Shape Change Technologies website.

Burkes et al, "Combustion Synthesis NiTi-TiC Composites with Controlled Porosity for Biomedical Applications", Materials Research Society, pp. 1-3, 2003.

Duerig et al., "Metals Superelastic Nitinol for Medical Devices", Medical Plastics and Biomaterials Magazine, MPB Article Index, pp. 1-7, Mar. 1997—printed from Medical Device Link website.

* cited by examiner

GUIDEWIRES INCLUDING A POROUS NICKEL-TITANIUM ALLOY

FIELD OF THE INVENTION

The present invention pertains to medical devices, and methods for manufacturing medical devices. More particularly, the present invention pertains to guidewires including a core wire, a tubular member, or both made from a porous nickel-titanium alloy.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices. An example medical device may include a guidewire. The guidewire may include an elongate shaft. The shaft may include a porous metal alloy. The porous metal alloy may be arranged so that the porous metal alloy has a first pore distribution along a first portion of the shaft and a second pore distribution different from the first pore distribution along a second portion of the shaft.

Another example guidewire may include an elongate core wire. A tubular member may be disposed over a portion of the core wire. The tubular member may have a plurality of slots formed therein. The tubular member may include a porous nickel-titanium alloy. The porous nickel-titanium alloy may include a first group of pores having a first configuration and a second group of pores having a second configuration different from the first configuration.

Another example guidewire may include an elongate shaft including a porous metal alloy. The shaft may include a first portion having a first pore distribution and a second portion having a second pore distribution different from the first pore distribution. The first pore distribution may provide the first portion with a first flexibility. The second pore distribution may provide the second portion with a second flexibility different from the first flexibility.

The above summary of some embodiments is not intended to describe each disclosed embodiment or every implementation of the present invention. The Figures and Detailed Description, which follow, more particularly exemplify these embodiments.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Figure 1:
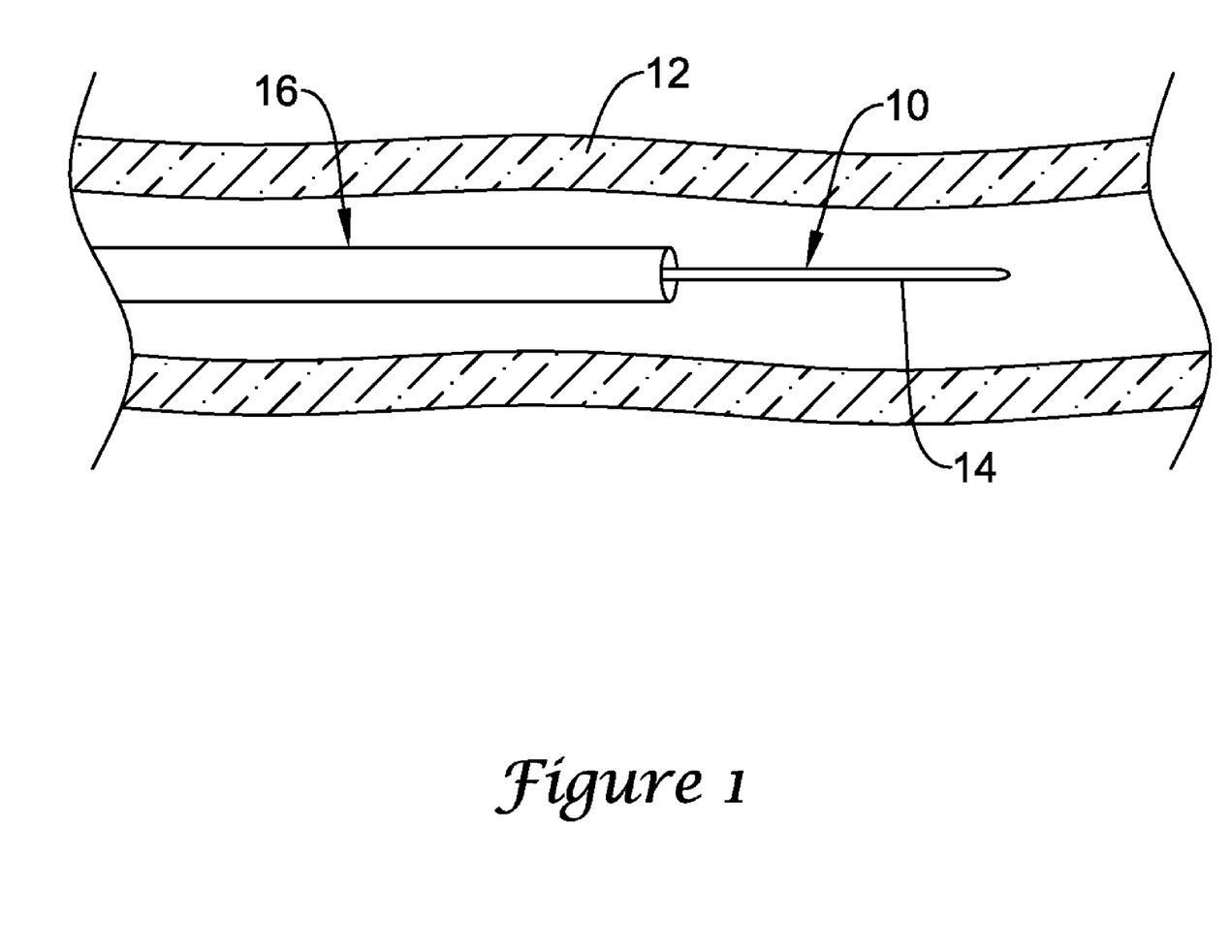
FIG. 1 is a plan view of an example medical device disposed in a blood vessel.

FIG. 1 is a plan view of an example medical device 10, for example a guidewire, disposed in a blood vessel 12. Guidewire 10 may include a distal section 14 that may be generally configured for probing within the anatomy of a patient. Guidewire 10 may be used for intravascular procedures. For example, guidewire 10 may be used in conjunction with another medical device 16, which may take the form of a catheter, to treat and/or diagnose a medical condition. Of course, numerous other uses are known amongst clinicians for guidewires, catheters, and other similarly configured medical devices.

Although medical device 10 is depicted in several of the drawings as a guidewire, it is not intended to be limited to being a guidewire. For example, medical device 10 may take the form of a suitable guiding, diagnosing, or treating device (including catheters, endoscopic instruments and/or endoscopes, laparoscopic instruments, stent delivery systems, embolic filter systems, urology stone retrieval systems, embolic coil delivery systems, atherectomy shafts, thermoctomy shafts, etc., and the like) and it may be suitable for use at various locations and/or body lumens within a patient. For example, medical device/guidewire 10 may be suitable for use in neurological interventions, coronary interventions, peripheral interventions, etc. As such, guidewire 10 may be appropriately sized for a given intervention. For example, guidewire 10 may have an outside diameter of about 0.0254 to about 12.7 mm (0.001 to about 0.5 inches), about 0.0381 to about 1.27 mm (0.0015 to about 0.05 inches), or about 0.254 to about 0.356 mm (0.010 to about 0.014 inches) for neurological interventions; an outside diameter of about 0.0254 to about 12.7 mm (0.001 to about 0.5 inches), about 0.254 to about 1.27 mm (0.01 to about 0.05 inches), or about 0.356 mm (0.014 inches) for coronary interventions; or an outside diameter of about 0.254 to about 12.7 mm (0.01 to about 0.5 inches, 0.508 to about 1.27 mm (about 0.02 to about 0.05 inches), or about 0.356 to about 0.965 mm (0.014 to 0.038 inches) for peripheral interventions. These dimensions, may vary depending on, for example, the type of device (e.g., catheter, guidewire, etc.), the anatomy of the patient, and/or the goal of the intervention. In some embodiments, for example, guidewire 10 may be a crossing guidewire that can be used to help a clinician cross an occlusion or stenosis in vessel 12.

Figure 2:
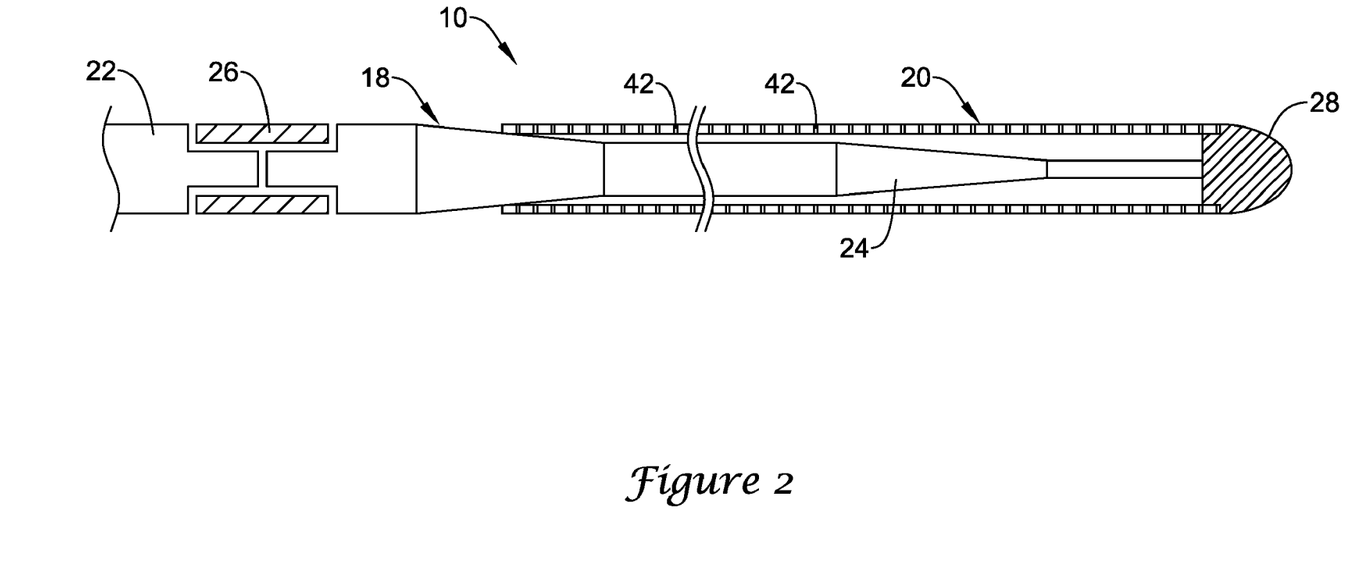
FIG. 2 is a partial cross-sectional view of an example medical device.

FIG. 2 is a partial cross-sectional view of guidewire 10. Here it can be seen that guidewire 10 may include a core member or core wire 18 and a tubular member 20 disposed over at least a portion of core wire 18. Core wire 18 may include a proximal section 22 and a distal section 24. A connector 26 may couple or otherwise attach proximal section 22 to distal section 24. Alternatively, core wire 18 may be a unitary member without a connector. A tip member 28 may also be coupled to core wire 18 and/or tubular member 20 that may define an atraumatic distal tip of guidewire 10. In some embodiments, tip member 28 may include a solder ball tip. Alternatively, tip member 28 may include a polymeric material. A coil (not shown) may be disposed in tubular member 20, for example adjacent tip member 28. In at least some embodiments, the coil may take the form of a radiopaque coil.

In at least some embodiments, tubular member 20 includes a plurality of cuts, apertures, and/or slots 42 formed therein. Various embodiments of arrangements and configurations of slots 42 are contemplated. In some embodiments, at least some, if not all of slots 42 are disposed at the same or a similar angle with respect to the longitudinal axis of the tubular member 20. As shown, slots 42 can be disposed at an angle that is perpendicular, or substantially perpendicular, to the longitudinal axis of tubular member 20 and/or can be characterized as being disposed in a plane that is normal to the longitudinal axis of tubular member 20. In various embodiments, slots 42 can be disposed at an angle that is not perpendicular to the longitudinal axis of tubular member 20, and/or can be characterized as being disposed in a plane that is not normal to the longitudinal axis of tubular member 20. Additionally, a group of one or more slots 42 may be disposed at different angles relative to another group of one or more slots 42. The distribution and/or configuration of slots 42 can also include, to the extent applicable, any of those disclosed in U.S. Pat. Publication No. 2004/0181174, the entire disclosure of which is herein incorporated by reference.

Slots 42 may be provided to enhance the flexibility of tubular member 20 while still allowing for suitable torque transmission characteristics. Slots 42 may be formed such that one or more rings and/or turns interconnected by one or more segments and/or beams are formed in tubular member 20, and such rings and beams may include portions of tubular member 20 that remain after slots 42 are formed in the body of tubular member 20. Such an interconnected ring structure may act to maintain a relatively high degree of torsional stiffness, while maintaining a desired level of lateral flexibility. In some embodiments, some adjacent slots 42 can be formed such that they include portions that overlap with each other about the circumference of tubular member 20. In other embodiments, some adjacent slots 42 can be disposed such that they do not necessarily overlap with each other, but are disposed in a pattern that provides the desired degree of lateral flexibility.

Additionally, slots 42 can be arranged along the length of, or about the circumference of, tubular member 20 to achieve desired properties. For example, adjacent slots 42, or groups of slots 42, can be arranged in a symmetrical pattern, such as being disposed essentially equally on opposite sides about the circumference of tubular member 20, or can be rotated by an angle relative to each other about the axis of tubular member 20. Additionally, adjacent slots 42, or groups of slots 42, may be equally spaced along the length of tubular member 20, or can be arranged in an increasing or decreasing density pattern, or can be arranged in a non-symmetric or irregular pattern. Other characteristics, such as slot size, slot shape and/or slot angle with respect to the longitudinal axis of tubular member 20, can also be varied along the length of tubular member 20 in order to vary the flexibility or other properties. In other embodiments, moreover, it is contemplated that the portions of the tubular member, such as a proximal section, or a distal section, or the entire tubular member 20, may not include any such slots 42.

As suggested above, slots 42 may be formed in groups of, for example, two, three, four, five, or more slots 42, which may be located at substantially the same location along the axis of tubular member 20. Within the groups of slots 42, there may be included slots 42 that are equal in size (i.e., span the same circumferential distance around tubular member 20). In addition, at least some slots 42 in a group may be unequal in size (i.e., span a different circumferential distance around tubular member 20). Longitudinally adjacent groups of slots 42 may have the same or different configurations. For example, some embodiments of tubular member 20 include slots 42 that are equal in size in a first group and then unequally sized in an adjacent group. It can be appreciated that in groups that have two slots 42 that are equal in size, the beams (i.e., the portion of tubular member 20 remaining after slots 42 are formed therein) are aligned with the center of tubular member 20. Conversely, in groups that have two slots 42 that are unequal in size, the beams are offset from the center of tubular member 20. Some embodiments of tubular member 20 include only slots 42 that are aligned with the center of tubular member 20, only slots 42 that are offset from the center of tubular member 20, or slots 42 that are aligned with the center of tubular member 20 in a first group and offset from the center of tubular member 20 in another group. The amount of offset may vary depending on the depth (or length) of slots 42 and can include a suitable distance based on the desired purpose of the guidewire 10.

Slots 42 can be formed by methods such as laser cutting (e.g., using a fiber laser), micro-machining, saw-cutting (e.g., using a diamond grit embedded semiconductor dicing blade), electron discharge machining, grinding, milling, casting, molding, chemically etching or treating, or other known methods, and the like. In some such embodiments, the structure of the tubular member 20 is formed by cutting and/or removing portions of the tube to form slots 42. Some example embodiments of appropriate micro-machining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720 and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 10 may include forming slots 42 in tubular member 20 using any of these or other manufacturing steps.

The materials that can be used for the various components of guidewire 10 may include those commonly associated with medical devices. For example, core wire 18, tubular member 20, connector 26, and/or tip member 28, and the like may be made from a metal, metal alloy, polymer (some examples of which are disclosed below), a metal-polymer composite, combinations thereof, and the like, or other suitable materials. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or other suitable materials.

Within the family of commercially available nickel-titanium or nitinol alloys, is a category designated "linear elastic" or "non-super-elastic" which, although similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2 through about 5 percent strain while remaining substantially elastic (e.g., before plastically deforming) whereas super elastic nitinol may accept up to about 8 percent strain before plastically deforming. Both of these materials can be distinguished from other linear elastic materials such as stainless steel (that can also can be distinguished based on its composition), which may accept only about 0.2 through about 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic mechanical thermal analysis (DMTA) over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature.

In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of core wire 18 and/or tubular member 20 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum or tantalum alloy, tungsten or tungsten alloy, polymer material loaded with a radiopaque filler, and the like. Additionally, other radiopaque marker bands and/or coils may also be incorporated into the design of guidewire 10 to achieve the same result.

In some embodiments, a degree of MRI compatibility is imparted into guidewire 10. For example, to enhance compatibility with Magnetic Resonance Imaging (MRI) machines, it may be desirable to make core wire 18 and/or tubular member 20, or other portions of the guidewire 10, in a manner that would impart a degree of MRI compatibility. For example, core wire 18 and/or tubular member 20, or portions thereof, may be made of a material that does not substantially distort the image and create substantial artifacts (i.e., gaps in the image). Certain ferromagnetic materials, for example, may not be suitable because they may create artifacts in an MRI image.

Core wire 18 and/or tubular member 20, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like.

Referring now to core wire 18, the entire core wire 18 can be made of the same material along its length, or in some embodiments, can include portions or sections made of different materials. In some embodiments, the material used to construct core wire 18 is chosen to impart varying flexibility and stiffness characteristics to different portions of core wire 18. For example, proximal section 22 and distal section 24 of core wire 18 may be formed of different materials, for example materials having different moduli of elasticity, resulting in a difference in flexibility. In some embodiments, the material used to construct proximal section 22 can be relatively stiff for pushability and torqueability, and the material used to construct distal section 24 can be relatively flexible by comparison for better lateral trackability and steerability. For example, proximal section 22 can be formed of straightened 304v stainless steel wire or ribbon and distal section 24 can be formed of a straightened super elastic or linear elastic alloy, for example a nickel-titanium alloy wire or ribbon.

In embodiments where different portions of core wire 18 are made of different materials, the different portions can be connected using any suitable connecting techniques and/or with connector 26. For example, the different portions of core wire 18 can be connected using welding (including laser welding), soldering, brazing, adhesive, or the like, or combinations thereof. These techniques can be utilized regardless of whether or not connector 26 is utilized. Connector 26 may include any structure generally suitable for connecting portions of a guidewire. One example of a suitable structure includes a structure such as a hypotube or a coiled wire which has an inside diameter sized appropriately to receive and connect to the ends of the proximal portion and the distal portion of the different portions of the core wire 18 being connected. A suitable configuration and/or structure can be utilized for connector 26 including those connectors described in U.S. Pat. Nos. 6,918,882 and 7,071,197 and/or in U.S. Patent Pub. No. 2006-0122537, the entire disclosures of which are herein incorporated by reference.

A sheath or covering (not shown) may be disposed over portions or all of core wire 18 and/or tubular member 20 that may define a generally smooth outer surface for guidewire 10. In other embodiments, however, such a sheath or covering may be absent from a portion of all of guidewire 10, such that tubular member 20 and/or core wire 18 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guidewire 10 (including, for example, the exterior surface of core wire 18 and/or the exterior surface of tubular member 20) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portions of core wire 18 and/or tubular member 20, or other portions of device 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. These and/or other polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The same may be true of tip member 28. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Often when designing a guidewire like guidewire 10, the ultimate material choices for the various components may amount to more than merely selecting from a list (e.g., such as lists above). This is because some of the materials listed above may not have the desired design features for the final guidewire and because the characteristics of one material may or may not work in concert with other materials. Furthermore, some of the materials listed above may have characteristics that are better suited for one component of guidewire 10 over another. Therefore, selecting materials for a guidewire by simply pulling from a list of materials may not result in a satisfactory final guidewire design.

Thus, guidewire designs may be the result of the careful selection of combinations of materials that may reduce manufacturing costs, reduce manufacturing time, aid in the intended intervention, and/or otherwise provide desirable benefits. For example, in some embodiments, tubular member 20 may be made from a tungsten alloy or a tantalum alloy. Tungsten alloys and tantalum alloys have a number of properties that may be desirable. For example, tungsten alloys and tantalum alloys are radiopaque. The radiopacity of tungsten alloys and tantalum alloys may obviate any need for a costly platinum coil. Additionally, because a radiopaque coil may be unnecessary due to the material selected to form the, for example, tubular member 20, the dimensions (and/or the manufacturing steps) of guidewire 10 can be reduced (e.g., the outer diameter can be decreased because space is no longer needed to house a radiopaque coil) allowing versions of guidewire 10 to be constructed for neurological intervention or other interventions where small size may be beneficial.

Other desirable characteristics of tungsten and/or tantalum alloys may include higher column strength and/or greater pushability (e.g., so that guidewire 10 may be a crossing wire), greater shapability, greater torque transmission, lower cost (as compared to nickel-titanium alloy), less post processing (as compared to nickel-titanium alloy, which may require a number of post processing steps), and the like. Other materials that may be utilized for similar reasons may include molybdenum-based alloys, high-speed tool steels, and metallic materials containing one or more heavy elements that make up about 30 or more weight percent.

While tungsten and tantalum alloys may be known for their desirable properties, they are also known to be brittle. Consequently, using these materials for tubular member 20, which may extend to a distal portion of guidewire 10 where heightened levels of flexibility may be desirable, may not be a practical design parameter. However, the arrangement of slots 42 in tubular member 20 may be such that the brittleness of the alloy can be sufficiently "softened" or otherwise overcome so that tubular member 20 can have both the desired radiopacity and the desired flexibility of a number of different interventions. For example, slots 42 may be widened and/or enlarged so that tubular member 20 may be sufficiently flexible.

In addition, using a tungsten or tantalum alloy may allow core wire 18 to be shortened or truncated. In some embodiments, core wire 18 may be completely omitted. These benefits may further lower the production costs of guidewire 10.

A number of additional material choices may also be made after some level of consideration. For example, core wire 18, tubular member 20, or both, or other suitable portion of guidewire 10, may include a porous material or alloy such as a porous nickel-titanium alloy. The porous nickel-titanium alloy may differ from traditional "non-porous" (e.g., having 0 percent or about 0 percent porosity, being solid, and/or being substantially solid and not purposefully manufactured to include pores) nickel-titanium alloys (e.g., nitinol) in that the pores in porous nickel-titanium alloy may be more prevalent, larger, and/or more densely arranged than traditional nitinol. Some example porous nickel-titanium alloys that may be suitable for use in core wire 18, tubular member 20, or both, are commercially available from Shape Change Technologies, Thousand Oaks, Calif. In some embodiments, porous forms of any of the other materials disclosed herein may also be used either alone or in combination with porous nickel-titanium alloys. Therefore, even though this disclosure makes reference to porous nickel-titanium alloys, this is not intended to limit embodiments of the present disclosure, rather, other suitable porous materials (e.g., any suitable porous metal and/or porous metal alloy) may be utilized.

In general, as the pore size (e.g., diameter and/or area of a given pore) and/or pore density (e.g., the number of pores per unit length or area) in a porous material is varied, the physical properties of the material may vary. For example, as the pore size and/or pore density increases, the flexibility of the material may increase. Consequently, variations in pore size and/or pore density can be utilized in guidewire 10 (e.g., core wire 18, tubular member 20, or both, or any other suitable portion of guidewire 10) to provide the desired structure with the desired physical characteristic (e.g., increased flexibility).

Figure 3:
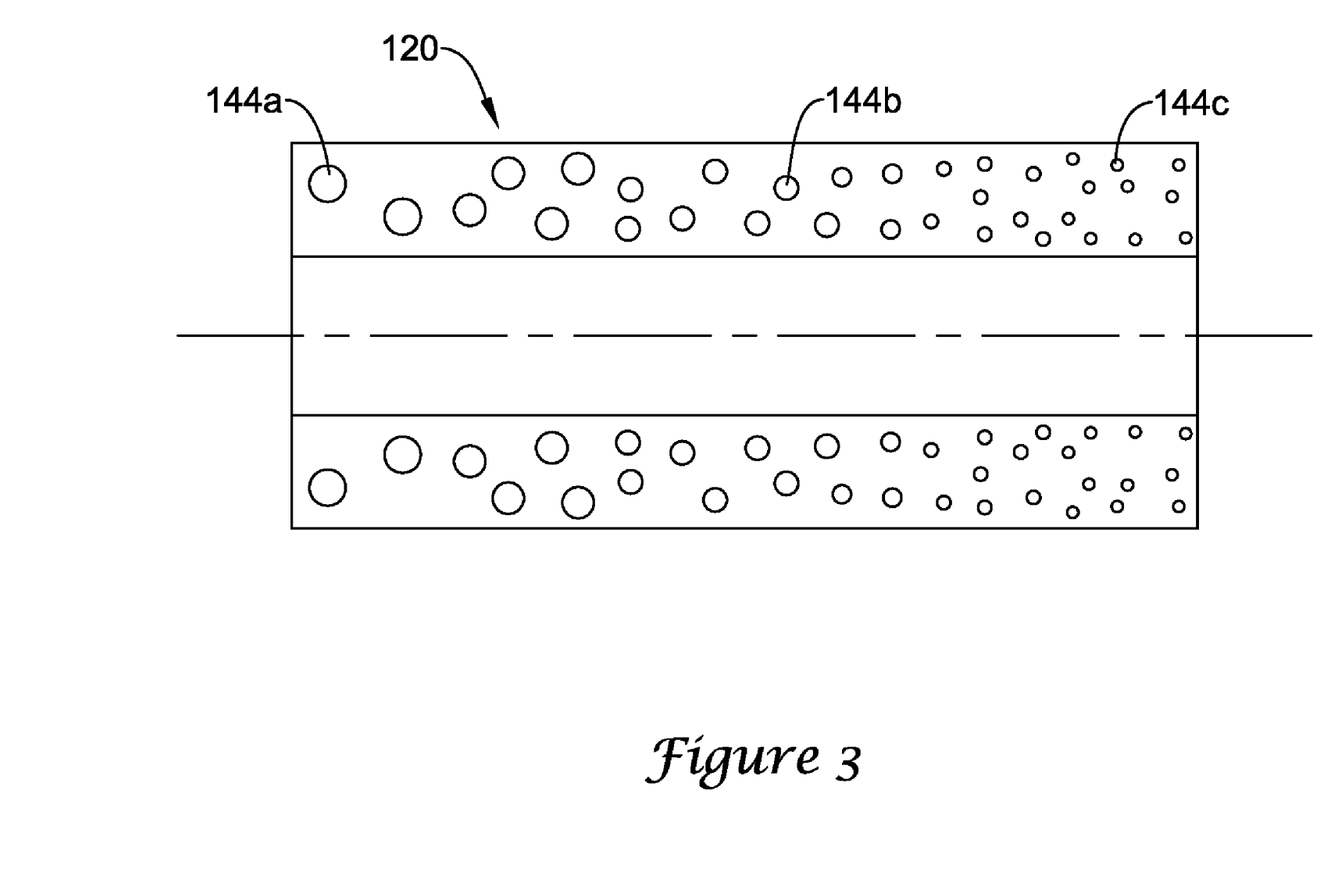
FIG. 3 is a side view of an example tubular member for use in a medical device.

Turning now to FIG. 3, an example tubular member 120 is illustrated that may be used in any of the guidewires disclosed herein. Tubular member 120 may include a number of pores, groups of pores, pore configurations, or pore distributions (bearing references numerals 144a/144b/144c, for example) that are disposed along the length (e.g., different portions or sections) of tubular member 120. These pores, groups of pores, pore configurations, or pore distributions may be disposed along differing portions of tubular member 120. In at least some embodiments, the pore size and/or pore density (also termed "porosity") may vary along the length of tubular member 120. For example, pores 144a may be larger than pores 144b, the latter being larger than pores 144c. The amount of variation in size between pores 144a and pores 144b may be about 1 to about 5 percent, or more than about 5 percent. Likewise, the variation in size between pores 144b and pores 144c may be about 1 to about 5 percent, or more than about 5 percent. Similarly, the variation in size between pores 144a and pores 144c may be about 1 to about 5 percent, or more than about 5 percent. In some embodiments, the larger pores (e.g., pores 144a) may be disposed at or closer to the proximal end of tubular member 120 and the smaller pores (e.g., pores 144c) may be disposed at or closer to the distal end of tubular member 120. This relative positioning of the different sized pores may provide greater lateral flexibility adjacent the distal end of tubular member 120. The reverse arrangement, of course, may also be utilized. Intermediately sized pores (e.g., pores 144b) may be disposed between pores 144a and pores 144c. It can be appreciated that other distributions of pore sizes may be utilized for tubular member 120.

The precise dimensions of pores 144a/144b/144c may vary considerably. The following dimension for pores 144a/144b/144c are provided for illustration purposes and are not intended to limit embodiments of the present disclosure. In some embodiments, the larger pores (e.g., pores 144a) may be about 5 to about 30 microns (μm) or about 10 to about 20 μm in diameter. The smaller pores (e.g., pores 144c) may be about 0.5 to about 10 μm or about 1 to about 5 μm in diameter. Intermediately sized pores (e.g., pores 144b) may be about 1 to about 20 μm or about 5 to about 10 μm in diameter.

In addition to differences in pore size, the porosity or pore density may also vary along the length of tubular member 120. For example, pores 144c may have a greater pore density or porosity than pores 144b, the latter having a greater pore density or porosity than pores 144a. In some embodiments, pores arranged with a greater density (e.g., pores 144c) may be disposed at or closer to the distal end of tubular member 120 and the pores having a lower density (e.g., pores 144a) may be disposed at or closer to the proximal end of tubular member 120. This may provide greater lateral flexibility adjacent the distal end of tubular member 120. The reverse arrangement, of course, may also be utilized. Pores having an intermediate pore density (e.g., pores 144b) may be disposed between pores 144a and pores 144c. It can be appreciated that other arrangements of pore densities and/or porosities may be utilized for tubular member 120.

The precise densities or porosities of pores 144a/144b/144c may vary considerably. The following densities or porosities for pores 144a/144b/144c are provided for illustration purposes and are not intended to limit the invention. In some embodiments, the pores arranged with a greater density (e.g., pores 144c) may account for about 20 to about 40 percent (e.g., about 30 percent or less) of the open surface porosity (cut area) of tubular member 120 at a given location. The pores having a lower density (e.g., pores 144a) may account for about 5 to about 20 percent (e.g., about 10 percent or less) of the open surface porosity of tubular member 120 at a given location. Pores having an intermediate pore density (e.g., pores 144b) may account for about 10 to about 30 percent (e.g., about 20 percent or less) of the open surface porosity of tubular member 120 at a given location.

Pores 144a/144b/144c that are found in a porous nickel-titanium alloy may have a number of suitable shapes. For example, pores 144a/144b/144c may be generally spherical (and/or circular) in shape as illustrated in FIG. 3. Alternatively, pores 144a/144b/144c may have a non-spherical (and/or non-circular) shape and/or other suitable geometric shape. In some embodiments, mixtures of geometries may be included in a porous nickel-titanium alloy. For example, a porous nickel-titanium alloy may include some pores that are generally spherical in shape and other pores having a non-spherical shape. The other pores disclosed herein may also vary in a similar manner.

Figure 4:
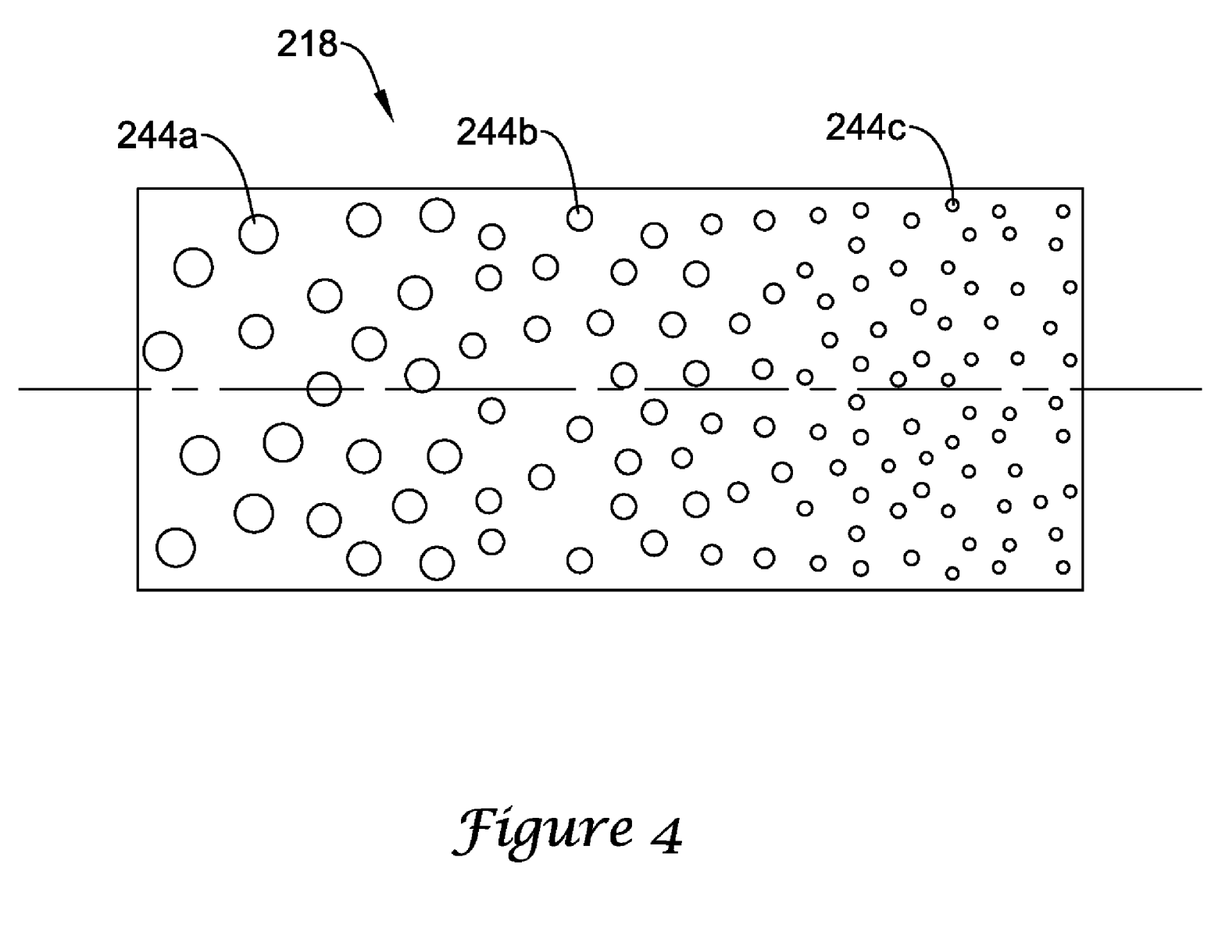
FIG. 4 is a side view of an example core wire for use in a medical device.

Just like tubular member 120, core wires may also include porous nickel-titanium alloy. For example, FIG. 4 illustrates an example core wire 218, which may be utilized in the embodiments of guidewires disclosed herein, includes pores, groups of pores, pore configurations, or pore distributions (bearing references numerals 244a/244b/244c, for example) that are disposed along the length of core wire 218. These pores, groups of pores, pore configurations, or pore distributions may be disposed along differing portions of core wire 218. Pores 244a/244b/244c may vary in a way analogous to how pores 144a/144b/144c vary as discussed herein with respect to FIG. 3. For example, pores 244a/244b/244c may vary in size (e.g., with pores 244a sized less than 244b sized less than 244c) and/or pore density (e.g., with the pore density or porosity of pores 244c less than 244b less than 244a). Of course, other suitable arrangement and/or distribution (including arrangements that are opposite what is shown) may be utilized.

Figure 5:
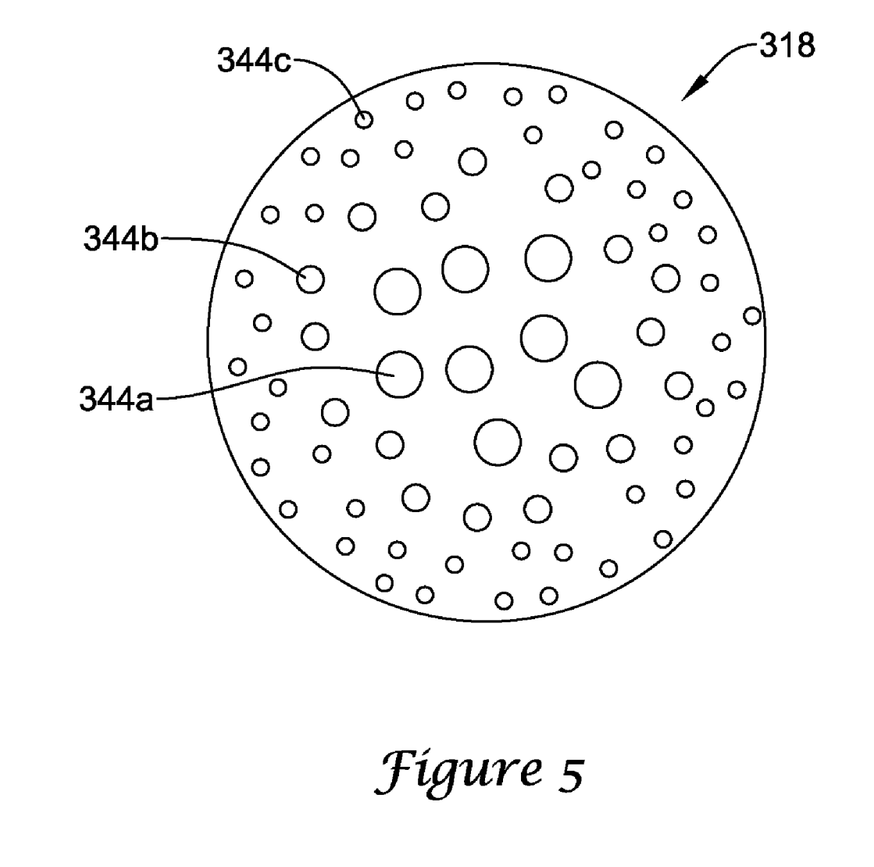
FIG. 5 is a cross-sectional view of another example core wire.

In addition to varying the porosity along the length, some example tubular members and/or core wires may also have a porosity that varies radially. For example, FIG. 5 illustrates an example core wire 318, which may be utilized in embodiments of the guidewires disclosed herein, that includes pores, groups of pores, or pore distributions (bearing references numerals 344a/344b/344c, for example) that vary radially. For example, pores 344a/344b/344c may vary in size radially (e.g., with pores 344a sized less than 344b sized less than 344c) and/or pore density (e.g., with the pore density or porosity of pores 344c less than 344b less than 344a). Of course, other suitable arrangement and/or distribution (including arrangements that are opposite what is shown) may be utilized.

Figure 6:
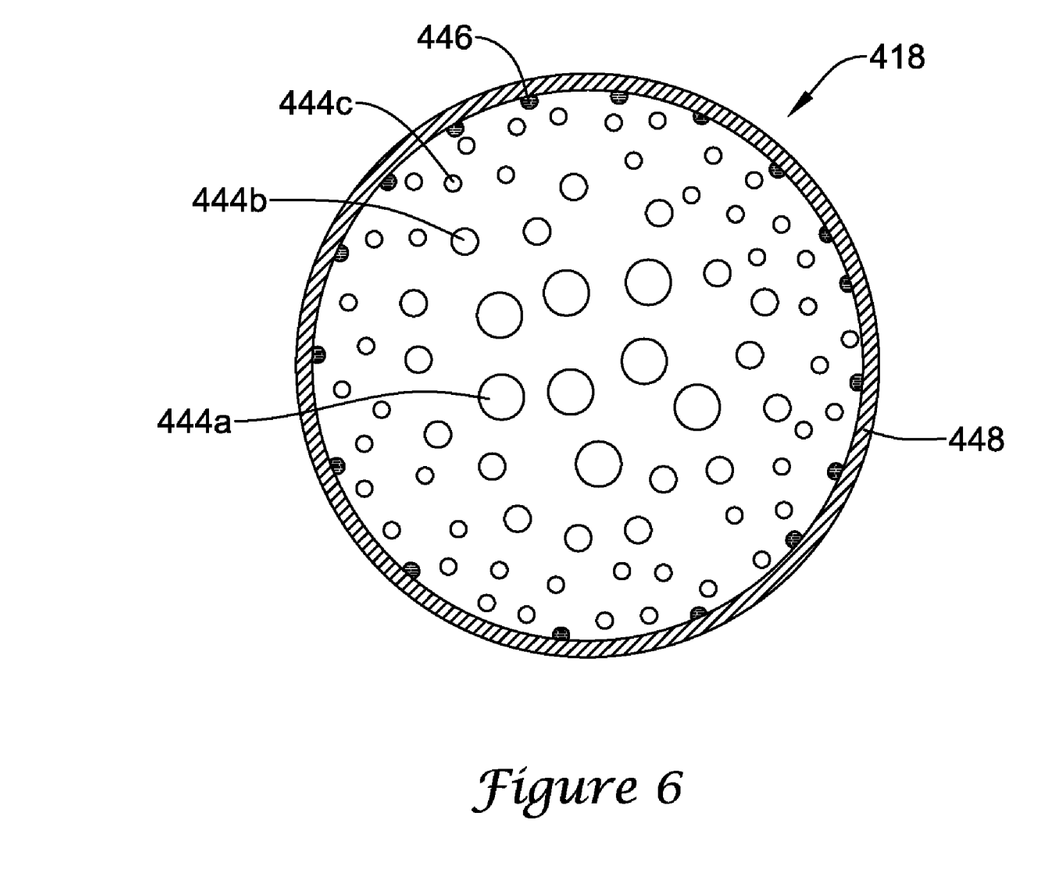
FIG. 6 is a cross-sectional view of another example core wire.

FIG. 6 illustrates an example core wire 418 that may be utilized with embodiments of the guidewires disclosed herein. Similar to core wire 318 discussed herein with respect to FIG. 5, guidewire 418 may include pores, groups of pores, pore configurations, or pore distributions (bearing references numerals 444a/444b/444c, for example) that vary radially. In addition, at least some of the pores, for example some of pores 444c such as those disposed along the exterior of core wire 18, may be impregnated with or otherwise filled with a radiopaque member or material 446, for example gold or other materials disclosed herein. Radiopaque member 446 may desirable to aid in the visualization of a guidewire that utilizes core wire 418. A sleeve or jacket 448, for example a hydrophilic jacket made from a suitable polymer disclosed herein, may be disposed along the exterior of core wire 418. Jacket 448 may help hold or seal the radiopaque member 446 in pores 444c.

It should be understood that this disclosure is, in many respects, only illustrative. Changes may be made in details, particularly in matters of shape, size, and arrangement of steps without exceeding the scope of the present disclosure. The present disclosure's scope is, of course, defined in the language in which the appended claims are expressed.

What is claimed is:

1. A guidewire, comprising:
an elongate shaft including a porous metal alloy, the shaft having a wall with a plurality of pores dispersed radially throughout;
wherein the plurality of pores are distributed throughout an axial cross-section of the shaft; and
wherein the porous metal alloy is arranged so that the porous metal alloy has a first pore distribution along a first portion of the shaft and a second pore distribution different from the first pore distribution along a second portion of the shaft, wherein the first portion of the shaft is disposed radially inward relative to the second portion of the shaft
wherein the first portion has a first flexibility and the second portion has a second flexibility different from the first flexibility.

2. The guidewire of claim 1, wherein the shaft includes a core wire.

3. The guidewire of claim 2, further comprising a tubular member disposed over a portion of the core wire, the tubular member having a plurality of slots formed therein.

4. The guidewire of claim 3, wherein the tubular member includes a tungsten alloy or a tantalum alloy.

5. The guidewire of claim 3, wherein the tubular member includes a porous nickel-titanium alloy.

6. The guidewire of claim 1, wherein the shaft includes a tubular member.

7. The guidewire of claim 6, wherein the tubular member has a plurality of slots formed therein.

8. The guidewire of claim 1, wherein the pores in the first pore distribution are larger than the pores in the second pore distribution.

9. The guidewire of claim 1, wherein the pores in the first pore distribution are arranged in a lower density than the pores in the second pore distribution.

10. The guidewire of claim 1, wherein at least some of the pores in the second pore distribution are filled with a radiopaque material.

11. The guidewire of claim 10, further comprising a polymer sleeve disposed over the pores in the second pore distribution.

12. The guidewire of claim 1, wherein the porous metal alloy includes a porous nickel-titanium alloy.

13. A guidewire, comprising:
an elongate core wire;
a tubular member disposed over a portion of the core wire, the tubular member having a plurality of slots formed therein;
wherein the tubular member includes a porous nickel-titanium alloy, wherein the porous nickel-titanium alloy includes a first group of pores having a first configuration and a second group of pores having a second configuration different from the first configuration, and wherein the first group of pores includes pores having a diameter of 0.5-10 microns; and
wherein the first group of pores are distributed through an axial cross-section of the tubular member
wherein the pores in the first configuration provide the tubular member with a first flexibility and the pores in the second configuration provide the tubular member with a second flexibility different from the first flexibility.

14. The guidewire of claim 13, wherein the core wire includes a porous nickel-titanium alloy.

15. The guidewire of claim 13, wherein the pores in the first configuration are larger than the pores in the second configuration.

16. The guidewire of claim 13, wherein the pores in the first configuration are arranged in a higher density than the pores in the second configuration.

17. A guidewire, comprising:
   an elongate shaft including a porous metal alloy;
   wherein the shaft includes a first portion having a first pore distribution and a second portion having a second pore distribution different from the first pore distribution, wherein the first pore distribution includes pores having a diameter of 5-30 microns;
   wherein the pores of the first pore distribution are distributed through an axial cross-section of the shaft; and
   wherein the first pore distribution provides the first portion with a first flexibility and the second pore distribution provides the second portion with a second flexibility different from the first flexibility.

* * * * *